(12) United States Patent
McClellan (10) Patent No.: US 8,439,936 B2
(45) Date of Patent: May 14, 2013

(54) DEVICE AND METHOD FOR TENDON, LIGAMENT OR SOFT TISSUE REPAIR

(75) Inventor: William Thomas McClellan, Morgantown, WV (US)

(73) Assignee: Zone 2 Surgical, Inc., Morgantown, WV (US)

( * ) Notice: Subject to any disclaimer, the term of this patent is extended or adjusted under 35 U.S.C. 154(b) by 955 days.

(21) Appl. No.: 12/273,109

(22) Filed: Nov. 18, 2008

(65) Prior Publication Data
US 2009/0228022 A1    Sep. 10, 2009

Related U.S. Application Data

(60) Provisional application No. 61/034,299, filed on Mar. 6, 2008.

(51) Int. Cl.
*A61B 17/08* (2006.01)
*A61B 17/04* (2006.01)

(52) U.S. Cl.
USPC ............. 606/151; 623/13.11; 623/13.14; 606/216; 606/217

(58) Field of Classification Search ........... 606/148, 606/150, 151, 153, 213, 215, 217, 232, 152, 606/216, 221, 222, 228, 313, 322, 323; 439/851, 439/866; 623/13.11, 13.12, 13.13, 13.14, 623/13.15
See application file for complete search history.

(56) References Cited

U.S. PATENT DOCUMENTS

| | | | |
|---|---|---|---|
| 3,541,591 A | 11/1970 | Hoegerman | |
| 3,570,497 A | 3/1971 | Lemole | |
| 3,664,345 A | 5/1972 | Dabbs et al. | |
| 3,976,079 A | 8/1976 | Samuels et al. | |
| 4,535,764 A | 8/1985 | Ebert | |
| 4,688,561 A | 8/1987 | Reese | |
| 4,741,330 A | 5/1988 | Hayhurst | |
| 4,750,492 A | 6/1988 | Jacobs | |
| 4,950,284 A | 8/1990 | Green et al. | |
| 4,950,285 A | 8/1990 | Wilk | |
| 4,971,075 A | 11/1990 | Lee | |
| 4,979,956 A | 12/1990 | Silvestrini | |
| 5,053,047 A | 10/1991 | Yoon | |
| 5,061,283 A | 10/1991 | Silvestrini | |
| 5,123,913 A | 6/1992 | Wilk et al. | |
| 5,207,694 A | 5/1993 | Broome | |
| 5,269,783 A | 12/1993 | Sander | |
| 5,314,436 A * | 5/1994 | Wilk | 606/153 |
| 5,318,566 A | 6/1994 | Miller | |

(Continued)

OTHER PUBLICATIONS

International Search Report and Written Opinion dated Jun. 18, 2010 for corresponding PCT Application PCT/US2009/064860.

*Primary Examiner* — Darwin Erezo
*Assistant Examiner* — Jing Ou
(74) *Attorney, Agent, or Firm* — Andrew D. Wright; Roberts Mlotkowski Safran & Cole, P.C.

(57) ABSTRACT

Disclosed are medical devices and methods for tendon, ligament, and soft tissue repair. A method includes introducing a first segment having a delivery assembly into a first soft tissue, and removing the delivery assembly to expose an opening of a hollow body of the first segment. The method also includes introducing a second segment having a second delivery assembly and a second body into a second soft tissue, guiding the second delivery assembly through the opening, and advancing the second body into the hollow body, thereby joining the first soft tissue and the second soft tissue.

23 Claims, 5 Drawing Sheets

U.S. PATENT DOCUMENTS

| | | | |
|---|---|---|---|
| 5,330,489 A | 7/1994 | Green et al. | |
| 5,356,412 A | 10/1994 | Golds et al. | |
| 5,356,417 A | 10/1994 | Golds | |
| 5,366,461 A | 11/1994 | Blasnik | |
| 5,382,257 A | 1/1995 | Lewis et al. | |
| 5,403,346 A | 4/1995 | Loeser | |
| 5,413,585 A | 5/1995 | Pagedas | |
| 5,462,542 A | 10/1995 | Alesi, Jr. | |
| 5,520,691 A | 5/1996 | Branch | |
| 5,549,122 A * | 8/1996 | Detweilwer | 128/898 |
| 5,591,206 A * | 1/1997 | Moufarrege | 606/215 |
| 5,643,295 A | 7/1997 | Yoon | |
| 5,665,109 A | 9/1997 | Yoon | |
| 5,704,372 A | 1/1998 | Moll et al. | |
| 5,766,218 A | 6/1998 | Arnott | |
| 5,810,853 A * | 9/1998 | Yoon | 606/151 |
| 5,850,674 A | 12/1998 | Jansen | |
| 5,860,948 A | 1/1999 | Buscemi | |
| 5,972,006 A | 10/1999 | Sciaino, Jr. | |
| 5,980,557 A | 11/1999 | Iserin et al. | |
| 5,984,933 A | 11/1999 | Yoon | |
| 6,007,576 A * | 12/1999 | McClellan | 623/23.64 |
| 6,014,792 A | 1/2000 | Marelin et al. | |
| 6,063,106 A | 5/2000 | Gibson | |
| 6,080,192 A | 6/2000 | Demopulos et al. | |
| 6,083,244 A | 7/2000 | Lubbers et al. | |
| 6,102,947 A | 8/2000 | Gordon | |
| 6,152,895 A | 11/2000 | Wilk | |
| 6,200,318 B1 | 3/2001 | Har-Shai et al. | |
| 6,485,504 B1 * | 11/2002 | Johnson et al. | 606/216 |
| 6,695,855 B1 * | 2/2004 | Gaston | 606/151 |
| 6,913,607 B2 * | 7/2005 | Ainsworth et al. | 606/151 |
| 6,926,730 B1 * | 8/2005 | Nguyen et al. | 606/213 |
| 6,942,668 B2 | 9/2005 | Padget et al. | |
| 6,951,561 B2 | 10/2005 | Warren et al. | |
| 6,984,241 B2 | 1/2006 | Lubbers et al. | |
| 7,008,428 B2 | 3/2006 | Cachia et al. | |
| 7,226,468 B2 | 6/2007 | Ruff | |
| 7,255,700 B2 | 8/2007 | Kaiser et al. | |
| 7,335,215 B2 * | 2/2008 | Buckman et al. | 606/153 |
| 7,361,179 B2 | 4/2008 | Rousseau et al. | |
| 7,455,683 B2 | 11/2008 | Geissler et al. | |
| 7,651,509 B2 | 1/2010 | Bojarski et al. | |
| 7,708,759 B2 | 5/2010 | Lubbers et al. | |
| 2002/0077631 A1 | 6/2002 | Lubbers et al. | |
| 2002/0161400 A1 | 10/2002 | Demopulos et al. | |
| 2002/0165561 A1 * | 11/2002 | Ainsworth et al. | 606/151 |
| 2004/0153104 A1 * | 8/2004 | Buckman et al. | 606/151 |
| 2004/0193217 A1 | 9/2004 | Lubbers et al. | |
| 2004/0267309 A1 * | 12/2004 | Garvin | 606/217 |
| 2005/0085833 A1 | 4/2005 | Gedebou | |
| 2005/0131430 A1 | 6/2005 | Ravikumar | |
| 2005/0149122 A1 * | 7/2005 | McDevitt et al. | 606/232 |
| 2006/0195103 A1 * | 8/2006 | Padget et al. | 606/72 |
| 2006/0276809 A1 | 12/2006 | Oliveira | |
| 2007/0021779 A1 | 1/2007 | Garvin et al. | |
| 2007/0055258 A1 | 3/2007 | Hansen | |
| 2009/0024216 A1 | 1/2009 | Cauthen, III et al. | |
| 2010/0268273 A1 | 10/2010 | Albertorio et al. | |
| 2011/0029001 A1 | 2/2011 | Trieu et al. | |

* cited by examiner

DEVICE AND METHOD FOR TENDON, LIGAMENT OR SOFT TISSUE REPAIR

CROSS REFERENCE TO RELATED APPLICATIONS

This application claims priority under 35 U.S.C. §119 to U.S. Provisional Application No. 61/034,299 filed on Mar. 6, 2008, the contents of which are incorporated herein by reference in their entirety.

BACKGROUND OF THE INVENTION

1. Field of the Invention

The invention generally relates to medical devices and procedures, and more particularly to devices and methods for tendon, ligament, and soft tissue repair, closure and/or reinsertion.

2. Discussion of Background Information

Conventional methods for tendon, ligament, and soft tissue repair often involve extensive suturing of the tissue being repaired. For example, in the case of tendon repair, one known method involves passing a first suture into and out of a first portion of the tendon numerous times, resulting in two free ends of the suture extending from the cut end of the first tendon portion. A second suture is similarly arranged in a second tendon portion. The free ends of the first and second sutures are tied (e.g., knotted) together to affix the cut ends of the tendon portions together.

However, such methods have numerous drawbacks. The act of passing the suture into and out of the tendon (e.g., typically at least six times per tendon portion) causes trauma to the tendon, thereby increasing the chance for infection. Furthermore repeated trauma to the tendon by excessive handling may create excessive damage to tendon/ligament/tissue vasculature which may compromise repair. Also, the knots of the sutures artificially increase the dimension of the tendon at the repair site, which creates increased friction at the repair site and/or tendon pulley interface. Increased friction at this interface increases the opportunity for tendon failure during loading. Even further, the strength of the repair is dependent upon the knots, which may slip over time (e.g., due to surgical error). Conventional suture-based repair methods may disadvantageously impair the vascularity of the tendon and have increased tendon diameter at the repair site. Traditional suture repair requires extensive exposure, manipulation, handling, and needle penetration of the tendon.

Barbed filaments provide an alternative to knot-based repair techniques. According to known methods, a single barbed filament is passed into and out of the portions of the tendon, thereby drawings the tendon portions together. Barbs on the exterior of the barbed filament engage the tendon portions internally, thereby resisting separation of the drawn-together tendon portions. Repairs using barbed filaments can be knotless, have the potential for a lower tendon profile at the site of the repair, and have the potential for equivalent strength when compared to knot-based repairs. However, techniques using barbed filaments can be more traumatic to the tendon than traditional repairs, may increase the risk of infection and/or impair the vascularity of the tendon, and are technically demanding.

Accordingly, there exists a need in the art to overcome the deficiencies and limitations described hereinabove.

SUMMARY

According to a first aspect of the invention, there is an apparatus for tissue repair comprising: a hollow body; an anchor at one end of the hollow body; a suture and needle connected to an other end of the hollow body opposite the anchor; and a second body. The hollow body is structured and arranged to be inserted in a first tissue comprising one of a first soft tissue and bone, and the second body is structured and arranged to be inserted in a second soft tissue. Moreover, the second body is structured and arranged to be inserted into and held within the hollow body, thereby connecting the first tissue and the second soft tissue.

In embodiments, the apparatus further comprises a second anchor connected to an end of the second body, and a second suture and second needle connected to an other end of the second body opposite the second anchor. In accordance with aspects of the invention, the suture and needle guide insertion of the hollow body into a sidewall of the first tissue and out of an end of the first tissue. Moreover, the second suture and second needle guide insertion of the second body into a sidewall of the second soft tissue, out of an end of the second soft tissue, and through the hollow body.

At least one of the hollow body and the second body may comprise pores (e.g., holes) and/or indentations that allow for in-growth of blood vessels or other connective tissue. In embodiments, the suture and needle are removable to expose an opening at the end of the hollow body.

The apparatus may further comprise an engagement structure on an interior of the hollow body. Additionally, the apparatus may include a second engagement structure on an exterior of the second body, wherein the second engagement structure corresponds with and engages the engagement structure when the second body is inserted into the hollow body. The apparatus may also comprise an anti-slipping structure on an exterior surface of the hollow body.

In embodiments, the anchor comprises a flange that is structured and arranged to engage an outer surface of the first soft tissue. The hollow body may be bent adjacent the anchor. The apparatus may further comprise a sleeve arranged between the second body and the hollow body frictionally securing the second body to the hollow body.

According to another aspect of the invention, there is a method for repairing soft tissue. The method includes: introducing a first segment comprising a delivery assembly into a first soft tissue, and removing the delivery assembly to expose an opening of a hollow body of the first segment. The method also includes introducing a second segment comprising a second delivery assembly and a second body into a second soft tissue, guiding the second delivery assembly through the opening, and advancing the second body into the hollow body, thereby joining the first soft tissue and the second soft tissue.

In embodiments, the removing the delivery assembly comprises cutting the first segment so that an opening of the hollow body is substantially flush with an end of the first soft tissue. The method may further comprise removing the second delivery assembly from the second body after one of: the guiding and the advancing.

In embodiments, the introducing the first segment comprises inserting the delivery assembly into a sidewall of the first soft tissue, through an interior of the first soft tissue, and out of an end of the first soft tissue. The introducing the first segment may further comprise advancing the hollow body through the first soft tissue until an anchor at one end of the hollow body engages the first soft tissue.

In accordance with aspects of the invention, the method may further comprise securing the first segment to the second segment. The securing may comprise engaging corresponding engagement structures on an interior of the hollow body and an exterior of the second body. The securing may comprise inserting a free end of the second segment into a sleeve, and moving the sleeve into a friction-fit position between the hollow body and the second body. The securing may comprises one of: deforming or melting corresponding portions of the hollow body and second body using heat, adhering the hollow body to the second body using adhesive, crimping the hollow body to the second body, and inserting a friction shim between the hollow body to the second body.

According to another aspect of the invention, there is an apparatus that connects and approximates a first soft tissue to a second soft tissue. The apparatus when installed in the first soft tissue and the second soft tissue includes a hollow elongate body comprising a first opening at a substantially straight end and a second opening at a bent end, wherein a first plane containing the first opening intersects a second plane containing the second opening. The apparatus also includes a first flange integral with the bent end, a second elongate body, a second flange integral with the second body, and a securing structure.

In an installed state, the hollow elongate body is arranged within the first soft tissue with the first flange anchoring the hollow elongate body in the first soft tissue. In the installed state, the second elongate body is arranged within the second soft tissue with the second flange anchoring the second elongate body in the second soft tissue. In the installed state, the second elongate body is arranged within the hollow elongate body, and the securing structure restricts motion of the second elongate body relative to the hollow elongate body. In embodiments, the securing structure may comprise, but is not limited to: one or more engagement structures on an interior surface of the hollow body and an exterior surface of the second body; a sleeve; a shim; a crimped portion; an adhered portion; and a heat deformed or melted portion.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

The invention generally relates to medical devices and procedures, and more particularly to devices and methods for tendon, ligament, and soft tissue repair. Exemplary embodiments of the invention comprise two cooperating segments that, after being inserted into respective soft tissue portions, engage each other to bring the soft tissue portions into contact with one another. According to aspects of the invention, the segments may be inserted into and anchored in the soft tissue portions in a minimally invasive (e.g., atraumatically) mode. Moreover, embodiments of the invention may be used to connect soft tissue to bone, such as, for example, a ligament to bone. In this manner, implementations of the invention provide an effective system and method for soft tissue repair that overcome the above-described deficiencies and limitations of the prior art.

Figure 1:
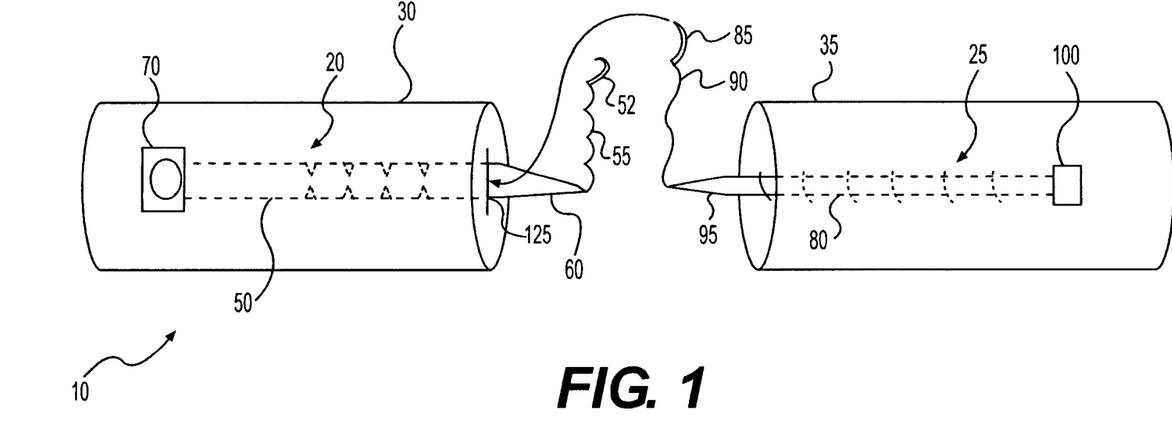
FIGS. 1-11 show elements of a system and method according to aspects of the invention.
Figure 2:
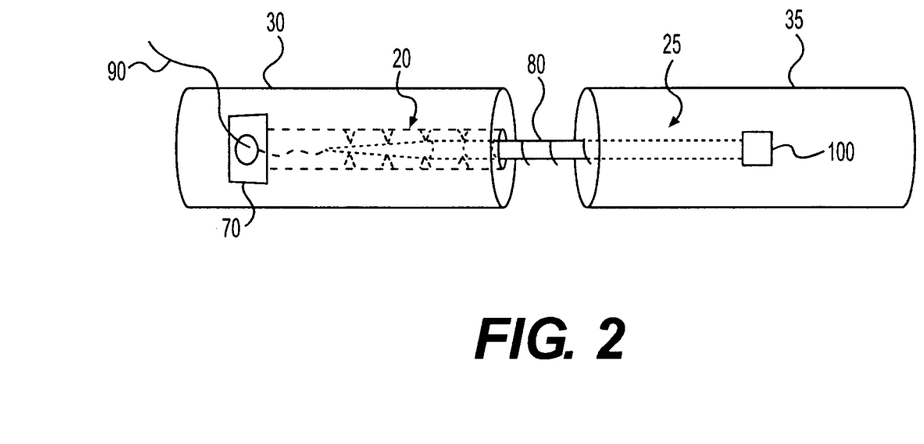
Figure 3:
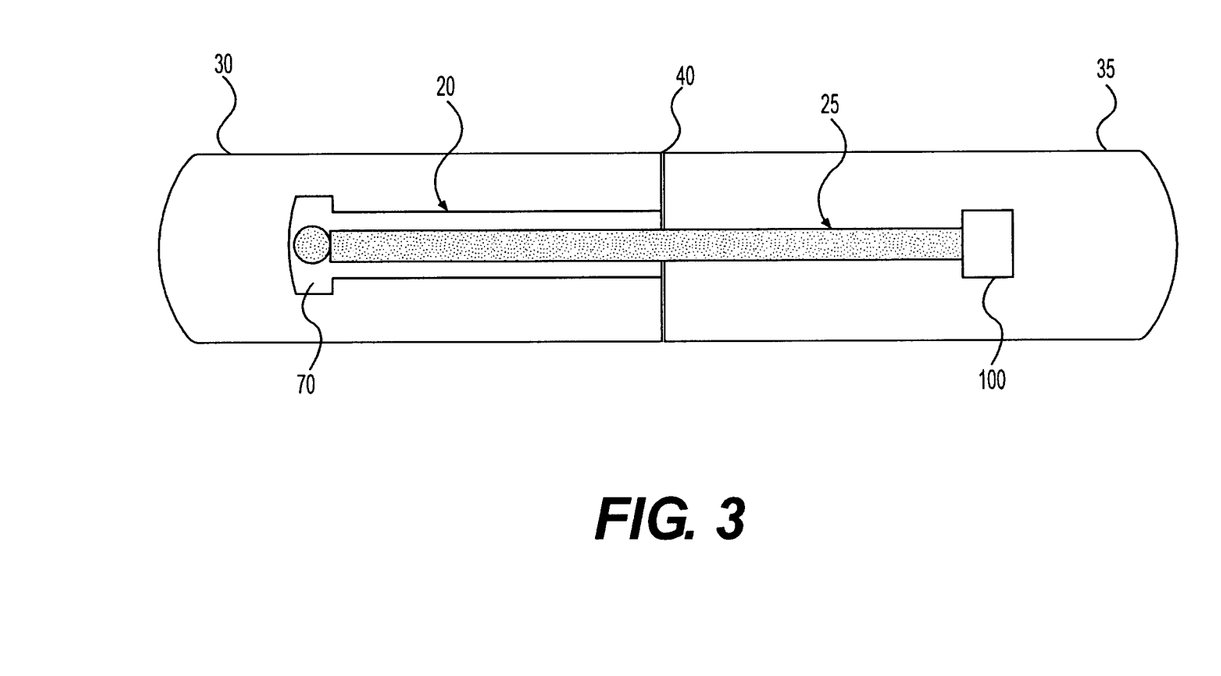

FIG. 1 shows a system 10 according to aspects of the invention including a female segment 20 and a male segment 25 for repairing of soft tissue (e.g., tendon, ligament, skin, etc.). In an exemplary implementation of the invention, the female segment 20 is inserted into a first tissue portion 30, and the male segment 25 is inserted into a second tissue portion 35. As depicted in FIG. 2, the male segment 25 may be drawn into the female segment 20, which draws the tissue portions 30, 35 together. FIG. 3 shows the system 10 in a substantially completed repair position, in which female segment 20 and male segment 25 are engaged such that the first tissue portion 30 and second tissue portion 35 abut one another at an interface 40.

Figure 4:
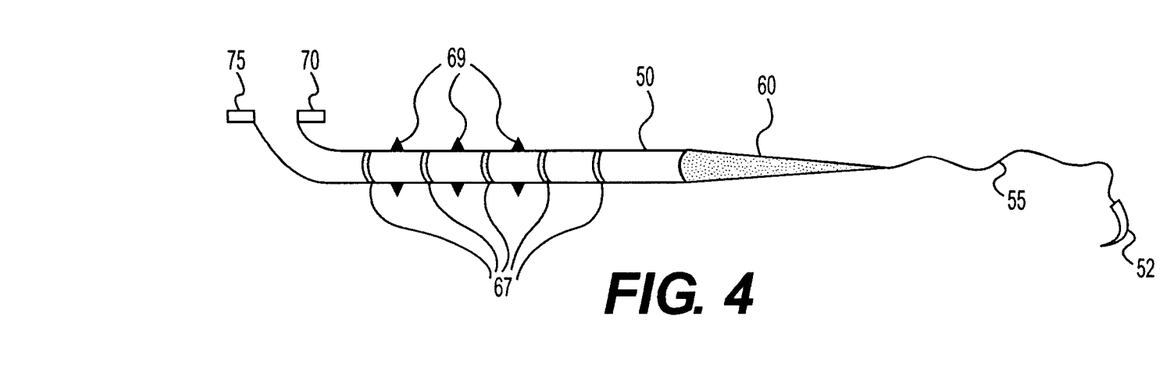

FIG. 4 shows further details of an exemplary female segment 20 according to aspects of the invention. In embodiments, the female segment 20 includes a hollow body 50 made of permanent (i.e., not absorbed by the body) or bio-absorbable material. Non-limiting examples of permanent material include plastic, nylon, etc. Non-limiting examples of bio-absorbable include monocryl, polydioxanone (PDS), etc. However, the invention is not limited to these examples, and any suitable materials may be used for forming the male and female segments. Moreover, each segment may be composed of a combination of different materials.

The female segment 20 further includes a delivery system at one end of the hollow body 50. The delivery system comprises a curved needle 52 swaged to one end of a suture 55. An opposite end of the suture 55 is integrally connected to an introducer wedge 60. The introducer wedge 60 may be in the shape of a cone (although other shapes may be used), and functions as a delivery wedge for atraumatically introducing the female segment 20 into soft tissue (e.g., tendon, ligament, etc.). In embodiments the introducer wedge 60 is solid and its base has substantially the same diameter as the outer diameter of the hollow body 50. The introducer wedge 60 is affixed to the hollow body 50, for example, via a seamless connection. The introducer wedge 60 may be made of the same material as the hollow body 45, or alternatively may be made of a different material. As discussed herein, the introducer wedge 60 is configured to be cut from the hollow body 45, and the introducer wedge 60, curved needle 52, and suture are referred to as a removable delivery assembly.

In one embodiment, the hollow body 50 includes at least one structure 67 on its interior surface for engaging the outer surface of the male segment 25. The structure 67 may comprise, for example, ridges, teeth, roughening, knurling, protrusions, indentations, etc. The structure 67 may be arranged at any desired location along the interior of the hollow body 50. Moreover, plural instances of the structure 67 may be located throughout the hollow body 50, for example, at regularly spaced (predetermined) intervals. In one example, a single structure 67 is arranged at one end of the hollow body 50, although the invention is not limited to this arrangement.

In an alternative embodiment, the hollow body 50 has a substantially smooth inner surface. In this embodiment, the female segment 20 engages the male segment 25 by way of a security cap and/or through the use of an adhesive, described in greater detail below.

Still referring to FIG. 4, the hollow body 50 may be provided with one or more protrusions 69 (e.g., anti-slipping structure) on its exterior surface. The protrusions 69 allow the female segment 20 to better adhere to the inner surface of the soft tissue into which it is inserted. The protrusions 69 may comprise, for example, ridges, teeth, roughening, knurling, protrusions, indentations, etc.

An end of the hollow body 50 opposite the introducer wedge 60 is provided with an anchor 70. The anchor 70 is a continuation of the hollow body 50 and comprises a flange 75 that is structured and arranged to reside outside or inside the soft tissue when the system is installed (see FIG. 5). The anchor 70 may be integral with the hollow body 50 (e.g., integrally formed via a molding manufacturing process). The anchor 70 has a hole though it which is a continuation of the interior portion of the hollow body 50. The anchor 70 is angled appropriately in relation to the hollow body 50 so that as tension is loaded on the system 10, the anchor 70 will remain low profile (with respect to the surface of the tendon) so as not to interfere with any pulley system associated with the tissue (e.g., a tendon pulley). For example, a plane of the flange 75 may be angled with respect to the longitudinal axis of the hollow body 50. As another example, a first plane containing the opening of the hollow body at the flange may be non-parallel to (e.g., intersecting with) a second plane containing the opening of the hollow body at the end opposite the flange. The angle may be provided, for example, by a bend 80 in the hollow body 50.

Figure 5:
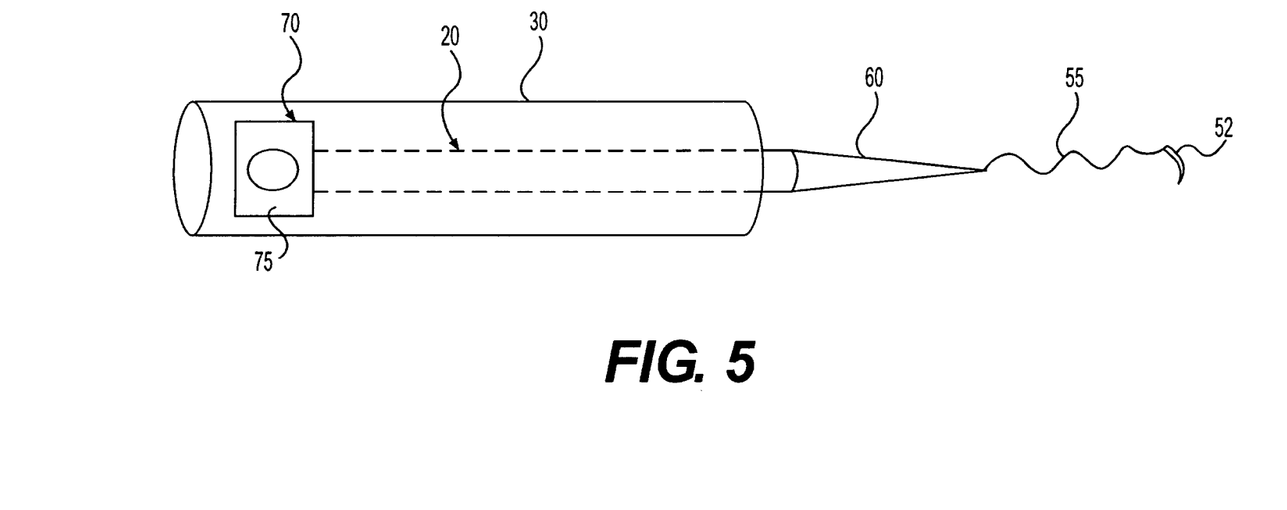

In embodiments, the anchor 70 functions to provide support for longitudinal, horizontal, and angular forces placed on the tendon/ligament system as it is loaded. The anchor 70 may or may not have small areas by which it may be sutured to the soft tissue. For example, the flange 75 may comprise one or more holes through which a suture may be passed. Additionally or alternatively, the anchor may be composed of a material that a suture can be inserted through without a pre-formed hole (e.g., pierced). The flange 75 may be any desired shape and configuration depending on the tissue, location, and anticipated load level (e.g., forces to be withstood). The anchor 70 may be made of the same material as the hollow body 50.

Figure 6:
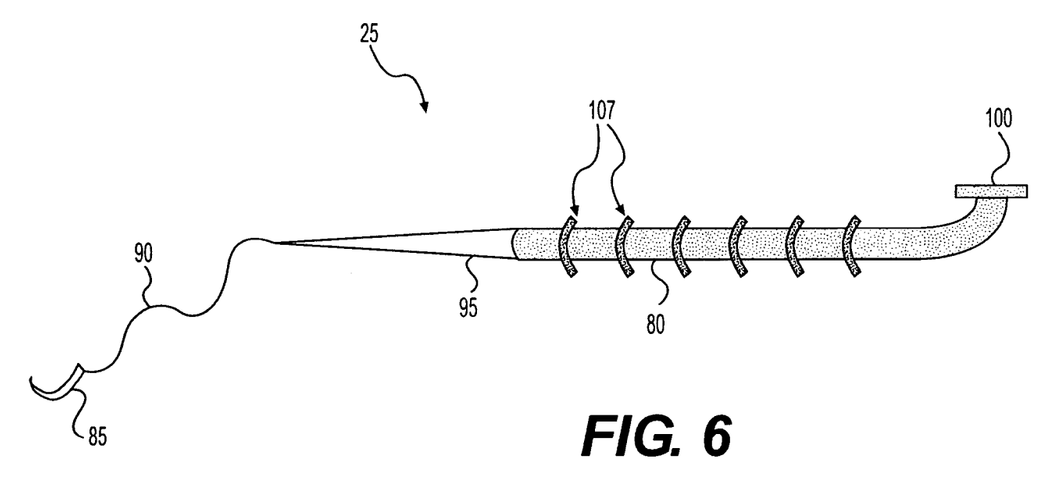

FIG. 6 shows further details of an exemplary male segment 25 according to aspects of the invention. In embodiments, the male segment 25 includes a solid body 80. Like the female segment 20, the male segment 25 includes a delivery system (e.g., removable delivery assembly) comprising a needle 85, suture 90, and introducer wedge 95. The introducer wedge 95 may comprise a solid cone, the base of which is affixed to an end of the solid body 80. At an opposite end of the solid body 80 is an anchor 100. In embodiments, the needle 85 is a curved tapered needle that is swaged to one end of the suture 90. Another end of the suture is integrally formed in (e.g., molded or melted into) an end of the introducer wedge 95. Moreover, the diameter of the base of the introducer wedge 95 equals the outer diameter of the solid body 80. The solid body 80, introducer wedge 95, and anchor 100 may be made of any of the aforementioned materials (or combinations of materials) described with respect to the hollow body 50.

Figure 7:
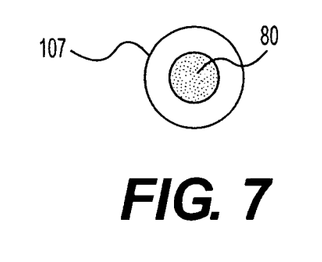
Figure 8:
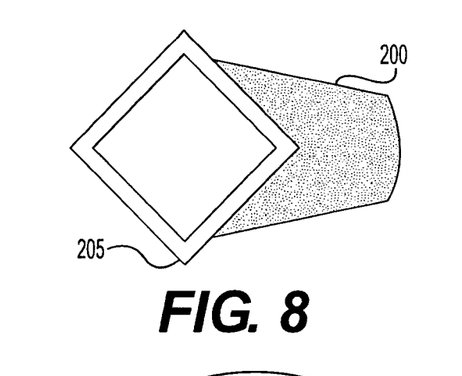
Figure 9:
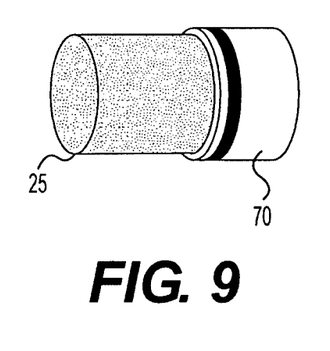
Figure 10:
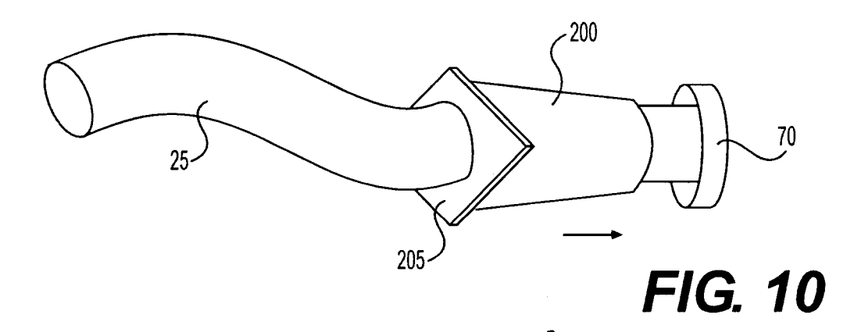
Figure 11:
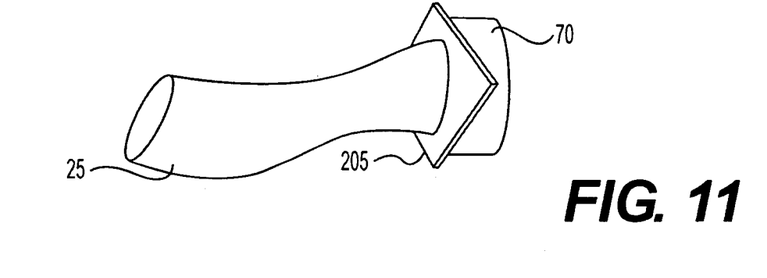

In one embodiment, at least one engagement structure 107 is arranged on the external surface of the solid core 80 (see FIG. 7). The engagement structure 107 may comprise, for example, ridges, teeth, roughening, knurling, protrusions, indentations, etc. The structure 107 may be arranged at any desired location along the interior of the solid body 80. Moreover, plural instances of the structure 107 may be located throughout the solid body 80, for example, at regularly spaced (predetermined) intervals. In one example, a single structure 107 is arranged at one end of the solid body 80, although the invention is not limited to this arrangement.

In embodiments, when the male segment 25 is inserted into the female segment 20 in a first direction, structure 107 engages structure 67 to prevent the male segment 25 from being removed out of the female segment 20 (e.g., in a second direction opposite the first direction). If multiple instances of structure 67 and/or structure 107 are used, then a ratchet-type connection can be made. That is, the male segment 25 can be inserted into the female segment 20 a little bit at a time, until a precise spatial relationship between the respective soft tissue parts is obtained.

In an alternative embodiment, the exterior surface of the solid body 80 is smooth. In this embodiment, the female segment 20 engages the male segment 25 by way of a security cap and/or through the use of an adhesive, described in greater detail below.

The anchor 100 of the male segment 25 is similar to the female segment, however, there is no hole in the middle. Instead, the anchor 100 is substantially solid and is positioned at an appropriate angle to reduce the overall extratendinous and/or intratendinous profile of the system 10. Like the anchor of the female segment, the anchor 100 may be of any suitable size and shape, and may provided with holes for suturing.

In an exemplary method according to aspects of the invention, the cut tendon, ligament, or tissue ends are freshened with a scalpel to optimize repair. The female needle 52 and suture 55 are delivered intratendinous (e.g., inserted into the sidewall of the tendon) starting at a distance of about one centimeter from the cut edge of the tissue. The needle 52 and suture 55 are passed through the interior of the tissue and passed out of the cut end of the tissue. After the suture 55 has been introduced in this manner, the introducer wedge 60 is pulled, using the suture 55, into and through the tendon or tissue with steady pressure until the anchor 70 engages the tendon or tissue and stops further advancement of the female segment 20. At this point, the female segment 20 is arranged in the tissue 30 as depicted in FIG. 1.

The female segment 20 may be cut flush in the plane of the tissue 30, for example as depicted at line 125 shown in FIG. 1. This cutting removes the introducer wedge 60, suture 55, and needle 52 from the hollow body 50. A portion of the hollow body 50 may also be removed by the cut, depending upon how far the female segment extends out of the tissue. This cutting exposes the hollow inner portion of the hollow body 50.

To deliver the male segment 25 into the other portion of 35 of the cut tissue, the male needle 85 and suture 90 are delivered in the tissue 35 in a manner similar to the delivery of the female needle and suture (e.g., inserted into the sidewall of the tissue about a centimeter back from the cut of the tissue). The needle 85 is extended out of the middle of the cut end of the tissue, and the suture 90 is pulled with steady pressure to pull the introducer wedge 95 and solid body 80 into the tissue 35. The solid body is pulled through the tissue 35 until the male anchor 100 engages the tissue and prevents further advancement. In this way, the male segment 25 is arranged in the tissue 35 as depicted in FIG. 1.

The needle 85 is removed, e.g., cut off of the suture 90, leaving a free end of the suture 90. The free end of the suture 90 is passed in a retrograde fashion through the exposed hollow body 50. More specifically, the free end of the suture 90 is inserted into the interior of the hollow body 50 at the cut 125. The free end of the suture 90 is advanced through the interior of the hollow body 50 until the free end of the suture 90 exits through the hole in the anchor 70. During, or after, this advancement of the free end of the suture 90, the cut ends of the tissue 30, 35 are approximated and the introducing wedge 95 is inserted into the interior of the hollow body 50 at the cut 125, as depicted in FIG. 2.

Pulling the free end of the suture 90 advances the solid body 80 into the hollow body 50. In one embodiment, advancement of the solid body 80 into the hollow body 50 causes structure 107 to engage structure 67, which prevents the male segment 25 from backing out of the female segment 20. When plural structures 107 and/or structures 67 are employed, the solid body 80 may be advanced in a ratchet-like fashion into the hollow body 50.

The male segment 25 is advanced into the female segment 30 until the cut ends of the tissue are well approximated and secure (see, e.g., FIG. 3). In some embodiments, a portion of the introducing wedge 95 and even the solid body 80 may extend out of the hole in the anchor 70. Any portion of the male segment 25 extending from the hole in the anchor 70 is cut away, such that the male segment 25 is flush with the female anchor 70 to give the system the lowest profile possible on the tissue surface to minimize interference (e.g., with a pulley associated with the tendon).

The invention is not limited to the exemplary method described herein. Instead, different processes may be practiced within the scope of the invention. For example, additional steps may be added, steps may be performed in a different order, etc.

In further embodiments, following cutting of the male segment 25, the end of the male segment 25 and the female anchor 70 may be additionally secured using a heat (e.g., to deform or melt at least one of the male segment and female anchor 70), adhesive (e.g., to adhere the male segment 25 and the female anchor 70), or by inserting a shim or wedge between the male segment 25 and the female anchor 70.

An additional system for securing the male segment 25 to the female segment 20 is shown in FIGS. 8-11. In this embodiment, a cap 200 sheathed over the free end of the male segment 25 that extends from the hole of the female anchor 70. The cap 200 may comprise, for example, a hollow cylindrical body that is slightly larger than the outer diameter of the solid body 80, and slightly smaller than the inner diameter of the hole at the female anchor 70. The cap 200 may further include a flange 205 of any suitable size and shape.

While the free end of the male segment 25 extends from the hole of the anchor 70 (e.g., before cutting), the cap 200 is slid over the free end of the male segment 25. The cap 200 is slid down the male segment 25 until an end of the cap 200 is advanced between the exterior of the male segment 25 and the interior of the hollow body 50. In this manner, the cap 200 acts as a wedge or shim that holds the male segment 25 in place by friction fit. The flange 205 prevents the cap from being pulled into the hollow body 50, should forces exerted on the male segment 25 exceed the friction fit.

The cap 200 can be used in addition to, or as an alternative to, the engagement structures 67, 107. After the cap 200 is set in place between the male segment 25 and the hollow body 50, the excess portion of the male segment 25 is cut flush with the female anchor portion 70. Optionally, the cap may be further secured by crimping (e.g., deforming at least one of the flange 205 and the flange 75), melting, or by applying adhesive (e.g., inserted between the male segment 25 and the cap 200 and/or between the cap 200 and the hollow body 50).

In further embodiments, at least one of the solid body 80 and hollow body 50 may be provided with pores (e.g., holes) and/or indentations having dimensions suitable to allow for ingrowth of blood vessels or other connective tissue into the system 10 to improve anchoring of the bodies within the soft tissue. The pores and/or indentations may be created by laser or other suitable device or manufacturing method.

The male and female segments may be sized to any suitable dimension. In one exemplary implementation of the invention, the female segment hollow body has an outer diameter of about 1 mm to about 3 mm, and the device has a total length of about 3 cm. However, the invention is not limited to these values, and any suitable dimensions may be used.

In yet further embodiments, at least one of the solid body 80 and hollow body 50 may be immunologically or chemically enhanced to regulate, modify, or supplement tendon, ligament, or soft tissue healing. For example, at least one of the solid body 80 and hollow body 50 may be coated or impregnated with growth hormone, antibiotic, etc.

According to additional aspects of the invention, portions of the male and female segments 20, 25 are flexible and soft, yet retain their prefabricated shape. For example, the hollow body 50, solid body 80, introducer wedges 60, 95, and anchors 70, 100 may be made of thermoset material that is soft and flexible yet retains its shape after being initially formed.

According to even further aspects of the invention, reinforcing fibers can be added to, or included in, at least one of the solid body 80 and hollow body 50. Such fibers may be incorporated into the elements of the system to provide structural reinforcement.

In accordance with further aspects of the invention, embodiments may be used to connect soft tissue to bone. For example, a hollow body 50 may be passed through a drill hole in bone, and a solid body 80 may be inserted into a soft tissue and then inserted into the hollow body 50. In this manner, embodiments of the invention may be used to restore a ligament-bone relationship.

In accordance with the soft tissue to bone implementation, a method may comprise: drilling a hole through a bone; inserting the delivery assembly of a hollow body through the hole in the bone; advancing the hollow body into the hole in the bone; and removing the delivery assembly to expose an opening of the hollow body. The method may further comprise steps similar to those already described herein, such as, for example: introducing and advancing a solid body into a soft tissue; passing a delivery assembly of the solid body through the hollow body; and advancing the solid body into the hollow body. In this manner, implementations of the invention provide a method for securing soft tissue to bone.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:
1. An apparatus for tissue repair, comprising:
a hollow body;
a first anchor at one end of the hollow body;
a first suture and a first needle connected to an other end of the hollow body opposite the first anchor; and
a second body that is a solid elongate body;

a second anchor connected to a solid end of the second body; and a second suture and a second needle connected to an other end of the second body opposite the second anchor;

wherein the first suture and the first needle are part of a delivery assembly that is removable from the hollow body to expose an opening at the other end of the hollow body;

in an installed state, the hollow body is structured and arranged to be within a first tissue with the first anchor contacting an exterior surface of the first tissue and anchoring the hollow body in the first tissue;

in the installed state, the solid elongate body is structured and arranged to be within a second soft tissue with the second anchor contacting an exterior surface of the second soft tissue and anchoring the solid elongate body in the second soft tissue;

in the installed state, and after removal of the delivery assembly, the second body is structured and arranged to be inserted into and held within the hollow body, thereby connecting the first tissue and the second soft tissue.

2. The apparatus of claim 1, wherein:

the first suture and the first needle are configured to guide insertion of the hollow body into a sidewall of the first tissue and out of an end of the first tissue, and the second suture and second needle are configured to guide insertion of the second body into a sidewall of the second soft tissue, out of an end of the second soft tissue, and through the hollow body.

3. The apparatus of claim 1, wherein at least one of the hollow body and the second body comprise at least one of pores and indentations that allow for in-growth of blood vessels or other connective tissue.

4. The apparatus of claim 1, further comprising an engagement structure on an interior of the hollow body.

5. The apparatus of claim 4, further comprising a second engagement structure on an exterior of the second body, wherein the second engagement structure corresponds with and engages the engagement structure when the second body is inserted into the hollow body.

6. The apparatus of claim 1, further comprising an anti-slipping structure on an exterior surface of the hollow body.

7. The apparatus of claim 1, wherein the first anchor comprises a flange that is structured and arranged to engage an outer surface of the first tissue, and at least one of the hollow body and the solid body is made of bio-absorbable material that is coated or impregnated with growth hormone or antibiotic.

8. The apparatus of claim 7, wherein an interior surface and an exterior surface of the hollow body are curved at a location that is adjacent the first anchor and also between the first anchor and the other end of the hollow body.

9. The apparatus of claim 1, further comprising a sleeve arranged between the second body and the hollow body frictionally securing the second body to the hollow body.

10. A method for repairing soft tissue using the apparatus of claim 1, comprising:

introducing a first segment comprising the hollow body and the delivery assembly into the first tissue;

removing the delivery assembly to expose the opening of the hollow body of the first segment;

introducing a second segment comprising a second delivery assembly and the second body into the second soft tissue;

guiding the second delivery assembly through the opening; and advancing the second body into the hollow body, thereby joining the first soft tissue and the second soft tissue.

11. The apparatus of claim 1, wherein:

the first suture and the first needle are connected to the other end of the hollow body by an introducer wedge that functions as a delivery wedge for atraumatically introducing the hollow body into the first tissue;

a dimension of a base of the introducer wedge equals an outer diameter of the hollow body; and the introducer wedge is part of the delivery assembly that is removable to expose the opening at the other end of the hollow body.

12. The apparatus of claim 1, wherein:

the first anchor has a hole through it which is a continuation of an interior portion of the hollow body; and the second anchor has no hole and is solid.

13. The apparatus of claim 12, wherein the first anchor comprises one or more additional holes configured for suturing the first anchor to the first tissue.

14. The apparatus of claim 12, further comprising:

an engagement structure on an interior of the hollow body; and a second engagement structure on an exterior of the second body, wherein the second engagement structure corresponds with and engages the engagement structure when the second body is inserted into the hollow body in the installed state, wherein the first anchor comprises a flange that is structured and arranged to engage the outer surface of the first tissue in the installed state; and the second anchor comprises a second flange that is structured and arranged to engage the outer surface of the second soft tissue in the installed state.

15. The apparatus of claim 1, further comprising:

a first engagement structure on an interior of the hollow body; and a second engagement structure on an exterior of the second body, wherein the second engagement structure corresponds with and engages the first engagement structure when the second body is inserted into the hollow body in the installed state;

wherein:

the first anchor comprises a flange that is structured and arranged to engage the outer surface of the first tissue in the installed state;

the second anchor comprises a second flange that is structured and arranged to engage the outer surface of the second soft tissue in the installed state;

the first suture and the first needle are connected to the other end of the hollow body by an introducer wedge that functions as a delivery wedge for atraumatically introducing the hollow body into the first tissue;

a dimension of a base of the introducer wedge equals an outer diameter of the hollow body;

the introducer wedge is part of the delivery assembly that is removable to expose the opening at the other end of the hollow body; and at least one of the solid body and the hollow body is immunologically or chemically enhanced to regulate, modify, or supplement tendon, ligament, or soft tissue healing.

16. An apparatus that connects and approximates a first soft tissue to a second soft tissue, the apparatus when installed in the first soft tissue and the second soft tissue comprises:

a hollow elongate body comprising a straight end and a curved end, a first opening at the straight end, and a second opening at the curved end;

a first flange integral with the hollow elongate body at the curved end;

a first suture and a first needle connected to the straight end of the hollow elongate body opposite the first flange, wherein the first suture and the first needle are part of a delivery assembly that is removable from the hollow elongate body to expose the first opening at the straight end of the hollow elongate body;

a solid elongate body;

a second flange integral with the solid elongate body; and a securing structure;

wherein, in an installed state, the hollow elongate body is configured to be arranged within the first soft tissue with the first flange contacting an exterior surface of the first soft tissue and anchoring the hollow elongate body in the first soft tissue, the solid elongate body is configured to be arranged within the second soft tissue with the second flange contacting an exterior surface of the second soft tissue and anchoring the solid elongate body in the second soft tissue in the installed state, the solid elongate body is within the hollow elongate body in the installed state, and the securing structure restricts motion of the solid elongate body relative to the hollow elongate body in the installed state.

17. The apparatus of claim 16, wherein:

the hollow elongate body comprises a bend along its length at the curved end;

the bend causes a plane of the first flange to be angled with respect to a longitudinal axis of the hollow body;

the hollow elongate body includes an interior surface within a hollow region; and the bend causes the interior surface to curve relative to the straight end at a location between the first opening and the first flange.

18. The apparatus of claim 17, further comprising:

a second suture connected to the solid elongate body at an end opposite the second flange; and a second needle connected to the second suture, wherein at least one of the solid elongate body and the hollow elongate body is immunologically or chemically enhanced to regulate, modify, or supplement tendon, ligament, or soft tissue healing.

19. An apparatus for tissue repair, comprising:

a hollow body;

a first suture and a first needle connected to a first end of the hollow body opposite a second end of the hollow body, wherein the first suture and the first needle are part of a delivery assembly that is removable from the hollow body to expose an opening at the first end of the hollow body; and a solid body comprising an anchor connected to a first end of the solid body and a second suture and second needle connected to an other end of the solid body opposite the anchor, wherein, in an installed state, the hollow body is structured and arranged to engage an exterior surface of a first tissue, the solid body is structured and arranged to be inserted in a second soft tissue with the anchor engaging an exterior surface of the second soft tissue in the installed state, and the solid body is structured and arranged to be inserted into and held within the hollow body in the installed state, thereby connecting the first tissue and the second soft tissue.

20. The apparatus of claim 19, wherein the second suture and second needle are configured to guide insertion of the solid body into the second soft tissue, out of the second soft tissue, and through the hollow body.

21. The apparatus of claim 20, further comprising:

a first engagement structure on an interior of the hollow body; and a second engagement structure on an exterior of the solid body, wherein the second engagement structure corresponds with and engages the first engagement structure when the solid body is within the hollow body.

22. The apparatus of claim 21, wherein:

the second suture and second needle are connected to the other end of the solid body by an introducer wedge; and a dimension of a base of the introducer wedge equals an outer diameter of the solid body.

23. The apparatus of claim 19, wherein:

the first end of the hollow body comprises a straight end and the second end of the hollow body comprises a curved end;

a flange is connected to the hollow body at the curved end of the hollow body;

solid body is structured and arranged to be inserted into the hollow body through the opening, after removal of the delivery assembly, to achieve the installed state, and at least one of the solid body and the hollow body is immunologically or chemically enhanced to regulate, modify, or supplement tendon, ligament, or soft tissue healing.

* * * * *